United States Patent [19]

Wirtz et al.

[11] Patent Number: 4,997,912
[45] Date of Patent: Mar. 5, 1991

[54] ESTERS OF FATTY ACIDS, WHICH MAY BE QUATERNIZED, FROM OXALKYLATED ALKYLALKYLENEDIAMINES

[75] Inventors: Herbert Wirtz, Eppstein; Hermann Hoffmann, Kelkheim; Werner Ritschel, Königstein/Taunus; Manfred Hofinger, Burgkirchen; Michael Mitzlaff, Bad Homburg; Dietrich Wolter, Liederbach, all of Fed. Rep. of Germany

[73] Assignee: Hoechst Aktiengesellschaft, Frankfurt am Main, Fed. Rep. of Germany

[21] Appl. No.: 284,988

[22] Filed: Dec. 15, 1988

[30] Foreign Application Priority Data

Dec. 18, 1987 [DE] Fed. Rep. of Germany ....... 3742935

[51] Int. Cl.$^5$ ................ C07C 219/06; C07C 219/12; C07C 219/18; C07C 219/22
[52] U.S. Cl. .................................... 530/232; 252/392; 260/404.5; 558/28; 558/207; 560/1; 560/122; 560/128; 560/193; 560/196; 560/221; 560/222; 560/251; 564/285; 564/286; 564/292; 564/294
[58] Field of Search ..................... 252/392; 260/404.5; 560/196, 1, 251, 128, 222, 122, 221, 193; 564/294, 285, 286, 292; 558/28, 207; 530/232

[56] References Cited

PUBLICATIONS

H. Marumo et al, *Chem. Abs.*, 69:20023n (1968).
Sekisui, Chem. Abstracts, vol. 95:204934d, 1981.

*Primary Examiner*—Vivian Garner
*Attorney, Agent, or Firm*—Connolly and Hutz

[57] ABSTRACT

Fatty acid esters of oxalkylated alkylalkylenediamines, which may be quaternized:
Esters of oxalkylated alkylalkylenediamines, which may be quaternized, of the formula

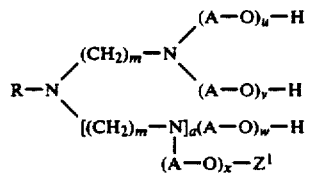

where the individual symbols have the meaning given in the description, process for their production and their use as corrosion inhibitors, particularly in crude oil recovery plants and crude oil treatment plants.

5 Claims, No Drawings

ESTERS OF FATTY ACIDS, WHICH MAY BE QUATERNIZED, FROM OXALKYLATED ALKYLALKYLENEDIAMINES

In technical processes in which metals come into contact with water or with two-phase oil/water systems, the danger of water corrosion exists. The danger is very high in the particular case of salt water systems, such as occur in crude oil recovery processes and crude oil treatment processes. The exploitation of a reservoir and the treatment of the crude oil is practically impossible without particular means of protection for the equipment used.

Corrosion inhibitors of this type are for example the aminoxethylates disclosed in U.S. Pat. No. 2,940,927, which, however, are not sufficiently effective in many instances. Further, U.S. Pat. No. 4,010,111 discloses the use of fatty acid amides as corrosion inhibitors for systems containing oxygen and U.S. Pat. No. 3,997,469 discloses the use of amides based on naphthenic acid. These agents are, however, not at all soluble or soluble only with difficulty, which considerably limits their effectiveness, since these materials are then present in the oil phase and the salt water can thus freely attack the iron. In JP-B No. 68/03 001 (Chem. Abstr. 69 (1968), 20023n) oxalkylated alkylalkylenediamines and their effect as corrosion inhibitors are disclosed. The effect of these compounds, however, is not as good as that of the esterified products which are described below.

The object of the invention was therefore to produce compounds of this kind which are effective as corrosion inhibitors in those water-in-oil emulsions, such as occur in crude oil recovery or crude oil treatment. A further object was to find those corrosion inhibitors which are present even in highly concentrated salt solution at least as a colloid dispersion. The invention relates to esters of oxalkylated alkylalkylenediamines, which may be quaternized, obtained by esterifying oxalkylated alkylalkylenediamines of the formula

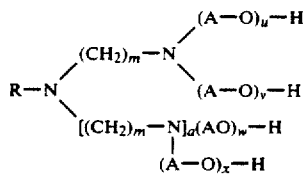

where R is a $C_8$-$C_{24}$-alkyl or a $C_8$-$C_{24}$-alkenyl, A is a group of the formula —$C_2H_4$— or —$C_3H_6$—, a is 0 or 1, m is 2 or 3, preferably 3, u,v,w and x are integers whose sum for the case a=0 is 3 to 30 and for the case a=1 is 4 to 40, with acids of the formula

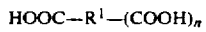

HOOC—$R^1$—(COOH)$_n$ where n=0 or is 1 and $R^1$ for the case n=0 is alkyl, alkenyl, cycloalkyl, cycloalkenyl having 5 to 35 carbon atoms in each instance or $R^1$ for the case n=1 is the residue of a dimeric fatty acid, and which may be subsequently quaternized by formation of groups of the formula $N^{\oplus}$-$R^2$ $M^{\ominus}$, where $R^2$ denotes $C_1$-$C_4$-alkyl or benzyl and $M^-$ is an anion, with the exception of compounds such as are obtained by esterification of oxalkylated alkylalkylenediamines of the formula

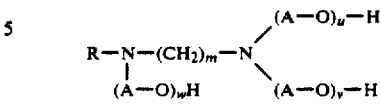

and are not quaternized. Esters which are preferred are those which are obtained by esterification with $C_{16}$-$C_{22}$-fatty acids, particularly with stearic acid, or with tall oil fatty acid, naphthenic acid or a dimeric fatty acid. The degree of oxethylation is preferably in the range 10 to 30 for the case a=0 and in the range 20 to 40 for the case a=1. Moreover a degree of oxethylation of 15 to 25 in the case a=0, a degree of oxethylation of 20 to 30 in the case a=1, is particularly preferred. Groups designated by —A—O may be selected from ethoxy and propoxy as well as mixtures of these, —$C_2H_4O$— being preferred. Anion M is preferably a halide anion, particularly chloride, a methosulfate or methophosphate anion.

The esters according to the invention are obtained by reacting oxethylated alkylalkylenediamines of the formula

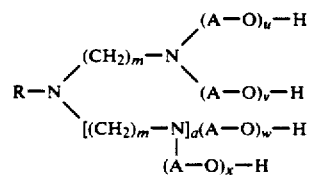

with an acid of the given formula. The reaction occurs in bulk or in high-boiling aromatic solvents using p-toluenesulfonic acid as catalyst at temperatures in the range 100° C. to 200° C. The molar ratio of monocarboxylic acid:aminoxethylate here is in the range 1:1 to 4:1. Accordingly, one, several or all —(A—O)—H groups are esterified. With dicarboxylic acids the molar ratio of dicarboxylic acid to aminoxethylate is in the range 0.5:1 to 1.5:1.

The oxalkylated alkylalkylenediamines used as the starting compounds are obtained under the normal conditions at about 120° C. to 160° C. from the amine and alkylene oxide by basic catalysis. The quaternization to introduce the $R^2$ radical is carried out by known processes, for example using methyl chloride, benzyl chloride or dimethyl sulfate in water or in isopropanol.

The invention relates to moreover the use of the esters of oxalkylated alkylalkylenediamines described above as corrosion inhibitors, including those compounds which are obtained by esterifying oxalkylated alkylalkylenediamines of the formula

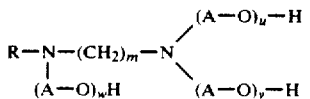

and are not quaternized.

These compounds are particularly suitable as corrosion inhibitors in crude oil recovery plants and in crude oil treatment plants which come into contact with salt water. The amounts used of these compounds as corrosion inhibitors are in the range 5 to 200, preferably 5 to 50 ppm, in the liquid medium.

The following examples are intended to explain the invention in more detail. The determination of the degree of oxethylation is carried out by titration of the basic nitrogen and by determination of the OH number. The progress of the esterification can be monitored by the quantity of water eliminated as well as by the acid number.

EXAMPLE 1

To a 1 liter 4-necked flask fitted with a stirrer, internal thermometer and distillation bridge are added 156.8 g (0.2 mol) of the addition product made from 1 mol of tallow alkyl propylenediamine and 10 mol of ethylene oxide having a molecular weight of 784. While stirring, addition is made over 10 minutes of 171 g (0.6 mol) tall oil fatty acid of molecular weight 285. The exothermic reaction is allowed to finish and the contents are then heated to 155°-180° C. In the course of 6 hours, about 6 to 10 ml of water distill off. The acid number drops simultaneously to less than 10. A brown viscous liquid is obtained.

EXAMPLE 2

To a 1 liter 4-necked flask fitted with a stirrer, internal thermometer and water separator are added 153.8 g (0.1 mol) of the reaction product made from tallow alkyl propylenediamine and 30 mol ethylene oxide having the molecular weight 1538 in 240 ml of an aromatic hydrocarbon. Addition is made over a period of 10 minutes of 85.5 g (0.15 mol) of a dimeric fatty acid of molecular weight 570, the exothermic reaction is allowed to finish and the contents are subquently heated to 155° C.-180° C. In the course of 6 to 8 hours, 5 ml of water are distilled off and a brown viscous product is obtained.

EXAMPLE 3

Using the process described in Example 1, 123 g (0.1 mol) of the addition product made from coconut-bis-(3-aminopropyl)-amine and 20 mol of ethylene oxide are initially introduced. The contents are heated to 50°-60° C., and 108 g (0.4 mol) stearic acid flakes of the molecular weight 270 are added in portions, the exothermic reaction is allowed to finish and the contents are subsequently heated to 155°-180° C. 5 ml of water are distilled off over a period of 6 to 8 hours and a brown viscous product is obtained.

EXAMPLE 4

Using the process as described in Example 1, 220 g (0.1 mol) of the addition product of tallow-bis-(3-aminopropyl)-amine and 40 mol ethylene oxide are added and mixed with 29.6 g (0.1 mol) of naphthenic acid. After the exothermic reaction has subsided, the mixture is kept at 155°-180° C. for 6 to 8 hours, during which about 2 ml of water are distilled over. The acid number drops simultaneously to below 3. A brown viscous liquid is obtained.

EXAMPLE 5

345 g of water are added to 320 g of the aminoxethylate ester produced as in Example 1 with stirring and the mixture is heated to 80° C. Dropwise addition of 50.6 g (0.4 mol) of benzyl chloride to this solution is carried out over a period of 30 minutes. On completion of the addition, the mixture is kept at the reflux temperature for 6 hours.

EXAMPLE 6

226 g of the aminoxethylate ester produced as in Example 3 are mixed with 60 g of isopropanol and quaternized using methyl chloride in an autoclave under the usual conditions at 60° C.

The products obtained according to Examples 1 to 6 have the following structure:

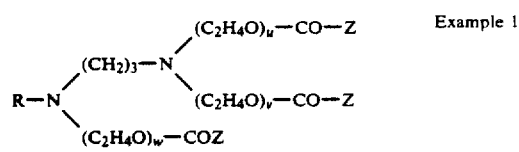

Example 1

R = tallow fatty alkyl, Z = alkyl radical from tall oil fatty acid, sum of u,v, and w = 10.

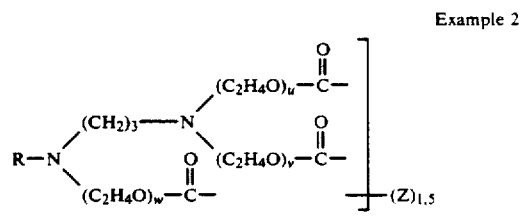

Example 2

R = tallow fatty alkyl, Z = alkyl radical from a dimeric fatty acid, sum of u,v, and w = 30.

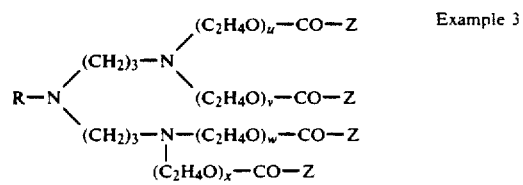

Example 3

R = alkyl derived from coconut oil fatty acid, Z = alkyl radical of stearic acid, sum of u,v,w, and x = 20.

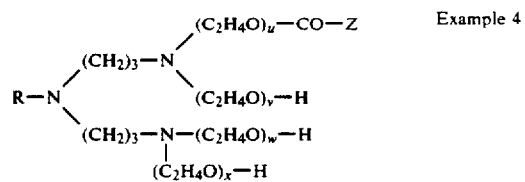

Example 4

R = tallow fatty alkyl, Z = alkyl radical from naphthenic acid, sum of u,v,w, and x = 40

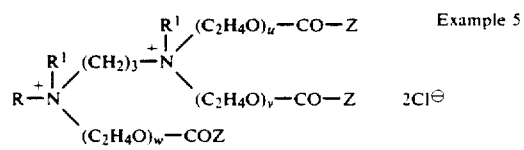

Example 5

R = tallow fatty alkyl, Z = alkyl radical of fatty acid derived from tall oil, sum of u,v and w = 10, $R^1$ = benzyl Example 6

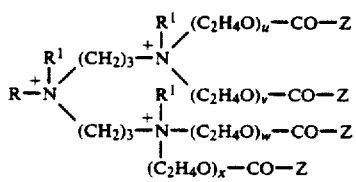

R=alkyl derived from fatty acids present in coconut oil, Z=alkyl radical of stearic acid, sum of u,v,w and z =20, $R^1$=methyl.

A dynamic test (the so-called "Wheel Test") was used to test the inhibitor compositions, a method by which the corrosion inhibitors for crude oil production and natural gas production are tested. A description of the method is to be found in the publication Materials Performance 21, Dec. 1982, pp. 45 to 47.

Steel sheets of dimensions 75 mm×10 mm×1 mm were selected as test specimens. The strips of sheet were rubbed with emery paper, de-greased with acetone and weighed. Salt water having 5% of dissolved NaCl was used as the test medium, with which additionally 10% by volume of freshly distilled kerosene was mixed. The pH of the aqueous solution was reduced to pH =3.5 using acetic acid in case of $CO_2$ absorption.

Before the beginning of the corrosion test, nitrogen was bubbled through both phases for half an hour, to drive off dissolved oxygen. Afterwards, either gaseous $CO_2$ or $H_2O$ was bubbled through both phases separately until saturation, but at least for 30 minutes.

Then 10,20 and 50 ppm of inhibitor were added, based on the volume of the test medium.

The degassed and weighed sheets were subsequently immersed in the emulsions and subjected for 24 hours at 670° C. to a mechanical displacement (40 cycles/minute by means of a shaft rotating the test vessels.

The test strips of sheet were subsequently cleaned mechanically and weighed after drying to determine the weight loss. The corrosion rates are given in mpy (mils per year) (39.4 mpy=1 mm/year). For comparison, a control value (test without addition of inhibitor) was determined.

The results obtained using this test method are summarized in the following table. The table contains protection values determined from weight losses in the presence of the compounds described in Examples 1 to 6. For comparison, data for a commercial product from Servo Co. are shown. A comparison of the protection values confirms the superiority of the products described according to the invention. The protection values shown in the following table are based on the control value for corrosion of 0.85 mm/a for the case of $CO_2$ corrosion and 0.71 mm/a for the case of $H_2S$ corrosion.

|  | $CO_2$ | | | $H_2S$ | | |
|---|---|---|---|---|---|---|
|  | 5 | 10 | 50 ppm | 5 | 10 | 50 ppm |
| Example | | | | | | |
| 1 | 61 | 78 | 82 | 77 | 80 | 93 |
| 2 | 71 | 79 | 80 | 68 | 77 | 86 |
| 3 | 68 | 82 | 83 | 73 | 82 | 95 |
| 4 | 58 | 64 | 78 | 83 | 86 | 94 |
| 5 | 64 | 73 | 76 | 64 | 77 | 91 |
| 6 | 75 | 78 | 84 | 68 | 74 | 96 |
| Servo CK 378 | 48 | 59 | 71 | 57 | 65 | 70 |

We claim:
1. An ester of oxalkylated alkylalkylenediamines, which may be quaternized, obtained by esterifying oxalkylated alkylalkylenediamines of the formula

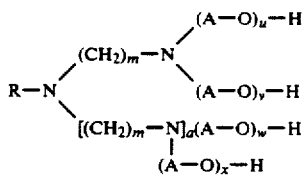

where R is a $C_8$-$C_{24}$-alkyl or a $C_8$-$C_{24}$-alkenyl, A is a group of the formula —$C_2H_4$— or —$C_3H_6$—, a is 0 or 1, m is 2 or 3, u,v,w and x are integers whose sum for the case a=0 is 3 to 30 and for the case a=1 is 4 to 40, with acids of the formula

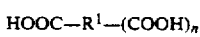

$$HOOC-R^1-(COOH)_n$$

where n=0 or is 1 and $R^1$ for the case n=0 is alkyl, alkenyl, cycloalkyl, cycloalkenyl having 5 to 35 carbon atoms in each instance or $R^1$ for the case n=1 is the residue of a dimeric fatty acid, and which may be subsequently quaternized by formation of groups of the formula $N^\oplus$-$R^2$ $M^\ominus$ where $R^2$ denotes $C_1$-$C_4$-alkyl or benzyl and $M^-$ is an anion, with the exception of compounds which are obtained by esterification of oxalkylated alkylalkylenediamines of the formula

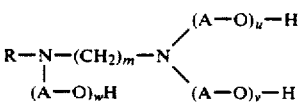

and which are not quanternized.

2. The ester of oxalkylated alkylalkylenediamines, which may be quaternized, as claimed in claim 1, wherein they are obtained by reaction with $C_{16}$-$C_{22}$-fatty acids, tall oil fatty acid or naphthenic acid or dimeric fatty acid.

3. The ester of oxalkylated alkylalkylenediamines, which may be quaternized, as claimed in claim 1, wherein M is a halide, methosulphate or methophosphate ion.

4. The esters of oxalkylated alkylalkylenediamines, which may be quaternized, as claimed in claim 1, wherein for the case a=0 the sum of the integers u, v, w is 10 to 30 and for the case a=1 the sum of the integers u, v, w and x is 20 to 40.

5. The ester of oxalkylated alkylalkylenediamines, which may be quaternized, as claimed in claim 1, wherein for the case a=0 the sum of the integers u, v, w is 15 to 25 and for the case a=1 the sum of the integers u, v, w and x is 20 to 30.

* * * * *

UNITED STATES PATENT AND TRADEMARK OFFICE
CERTIFICATE OF CORRECTION

PATENT NO. : 4,997,912
DATED : MARCH 5, 1991
INVENTOR(S) : WIRTZ ET AL

It is certified that error appears in the above-identified patent and that said Letters Patent is hereby corrected as shown below:

Col. 1, lines 15/16: "aminoxethylates" should read --amineethoxilates--.

Col. 2, line 52: "The invention relates to moreover" should read --The invention moreover relates to--.

Col. 5, line 37: "degassed" should read --degreased--.

Col. 5, line 39: "670°C" should read --70°C--.

Signed and Sealed this

Thirteenth Day of October, 1992

Attest:

DOUGLAS B. COMER

Attesting Officer

Acting Commissioner of Patents and Trademarks